(12) United States Patent
Becker

(10) Patent No.: US 8,821,719 B2
(45) Date of Patent: Sep. 2, 2014

(54) ARRANGEMENT FOR CONNECTION OF A MEDICAL DEVICE TO A WATER LINE

(75) Inventor: Franz Ferdinand Becker, Rodgau (DE)

(73) Assignees: Franz Ferdinand Becker, Rodgau (DE); Manfred Volker, Blankenbach (DE)

( * ) Notice: Subject to any disclaimer, the term of this patent is extended or adjusted under 35 U.S.C. 154(b) by 1177 days.

(21) Appl. No.: 12/088,700

(22) PCT Filed: Nov. 7, 2007

(86) PCT No.: PCT/DE2007/001999
§ 371 (c)(1),
(2), (4) Date: Mar. 31, 2008

(87) PCT Pub. No.: WO2008/074282
PCT Pub. Date: Jun. 26, 2008

(65) Prior Publication Data
US 2010/0219114 A1    Sep. 2, 2010

(30) Foreign Application Priority Data

Dec. 21, 2006  (DE) .................... 10 2006 060 611

(51) Int. Cl.
*B01D 61/32* (2006.01)
*A61M 1/16* (2006.01)

(52) U.S. Cl.
CPC ............ *A61M 1/168* (2013.01); *A61M 1/169* (2013.01)
USPC .......... 210/90; 210/137; 210/646; 210/257.2; 210/120; 210/121

(58) Field of Classification Search
CPC ........................... A61M 1/168; A61M 1/169
See application file for complete search history.

(56) References Cited

U.S. PATENT DOCUMENTS 5,624,551 A * 4/1997 Baumann et al. ............. 210/134
2004/0195157 A1 * 10/2004 Mullins et al. ................. 210/90

* cited by examiner

*Primary Examiner* — Dirk Bass
(74) *Attorney, Agent, or Firm* — Hammer & Associates, P.C.

(57) ABSTRACT

The arrangement for connection of a medical device, particularly a dialysis device, to a permeate line for the supply of permeate into the device is characterized by an adapter comprising a first supply line section with a terminal coupling member for connection to the water line, a pressure sensor and two successively arranged shut-off valves, and two second supply line sections that branch off from the first supply line member by means of a branching member. Both second supply line sections are connected to two different lines of the device in such a manner that disinfection fluid flows through both second supply line sections in a disinfection process of the device.

8 Claims, 2 Drawing Sheets

Figure 1:
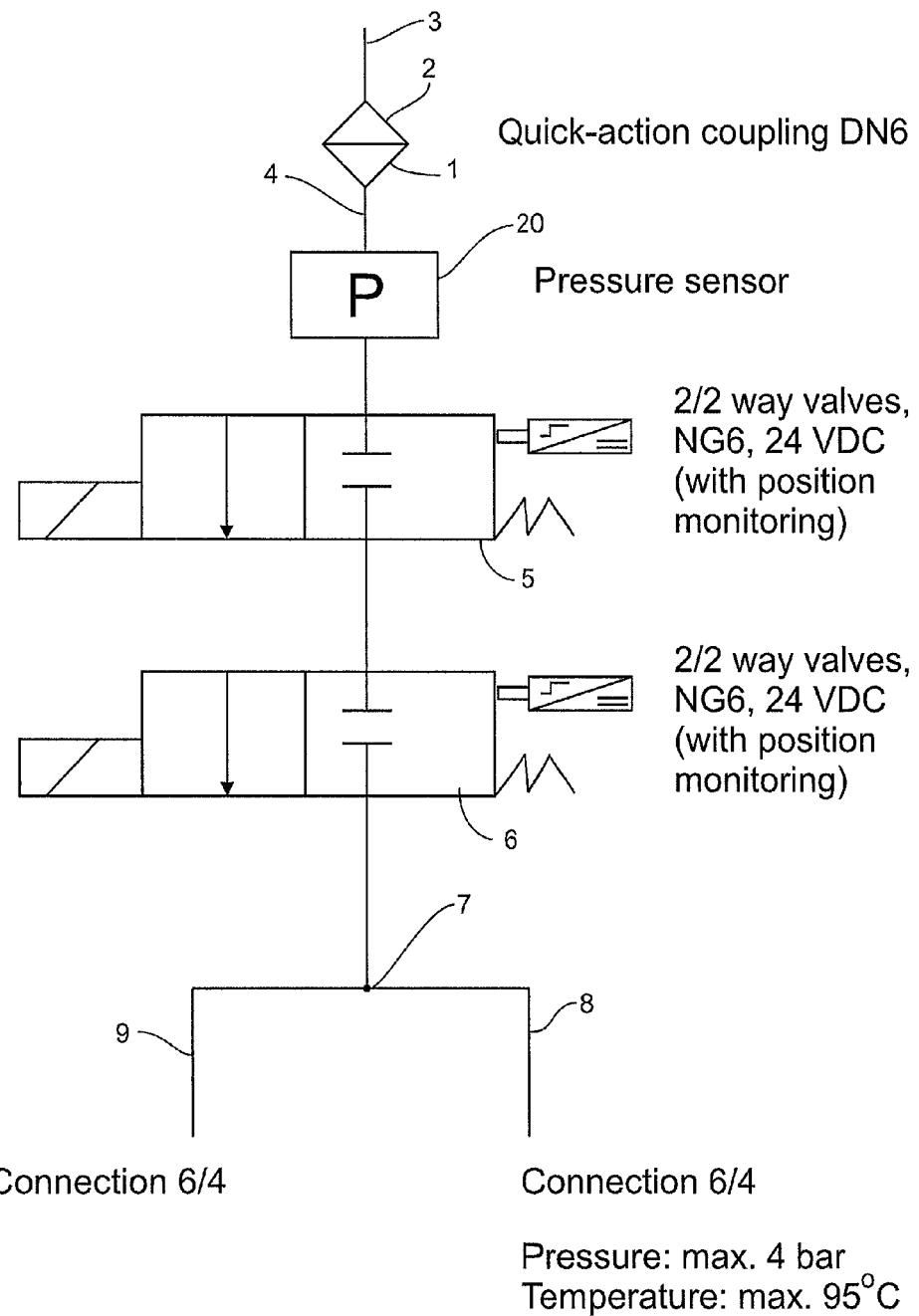

ARRANGEMENT FOR CONNECTION OF A MEDICAL DEVICE TO A WATER LINE

The present invention relates to an arrangement for connection of a medical device to a water line for the supply of water or prepared water into the device.

The present invention generally relates to a connection arrangement for medical devices that must be fed with water or prepared water for their operation. To be more specific, the present invention relates to a connection arrangement for those medical devices that in an online operation prepare the application solution required for treatment from prepared water and from a concentrate by mixing the same, as is above all the case with dialysis devices.

The invention shall now be explained in connection with dialysis devices.

The connection of such a device may be designed as a single connection or, however, as a connection to a ring line to which several dialysis devices are connectable.

The fluid components used in a dialysis operation must be clean by all means because any contamination in the dialysis fluid would endanger the patient treated. Bacteria, toxins and fungal spores in the dialysis fluid can be life-threatening. In the monitored industrial manufacture of the dialysis concentrates from which the dialysis fluid is made by being mixed with prepared water or permeate in the dialysis device, a situation must be ruled out where such contamination passes into the products. If it nevertheless occurs in the dialysis fluid, as has so far unfortunately happened in practice, this is bound to occur during preparation of the ready-for-use dialysis fluid.

Non-disinfected line sections in or on the dialysis device are a major cause for the contamination of dialysis fluid. This includes the permeate supply line between the dialysis device and the single connection for permeate or the permeate ring line. This permeate supply line is not included in the disinfection of the dialysis device in the formerly known connection systems, so that dangerous impurities generated by bacteria, toxins and fungal spores may form and collect.

It is the object of the present invention to provide an arrangement for connection of a medical device to a water supply line, in which or by which the above-described danger is prevented.

This object is achieved according to the invention by the features of patent claim 1.

Advantageous developments of the invention are characterized in the sub-claims.

According to the invention an adapter is used for connection of the device, the adapter comprising a first supply line section with a terminal coupling member for connection to an associated coupling member of the water line or permeate line, a downstream pressure sensor and two successively arranged shut-off valves, a branching member, preferably a Y-line section, being mounted on the other end of the first supply line section for dividing the first supply line section into two second supply line sections. Said two second supply line sections are connected to two different lines of the device in such a manner that in a disinfection mode of the device the disinfection fluid flows through the two second supply line sections while the two position-monitored shut-off valves are closed. Said second supply line sections are expediently formed by hoses which are mounted on the Y-member and can be connected with fixed hose connections, preferably hose clips, to the two lines of the device.

In further details, it is suggested that one of the two second line sections should be connected to the water inlet line of the device leading to the feed container for the permeate, and that the other second supply line section should be connected to another line of the device through which disinfection fluid is flowing in the disinfecting process.

With this configuration the disinfection fluid will flow in a disinfecting process of the device and with correspondingly actuated valves not only through the two second supply line sections of the connection system according to the invention, whereby the two second supply line sections are integrated into the disinfection circuit of the device, but this is also true for the water inlet line of the device leading to the feed container, which in a conventional device is not included in the disinfection circuit.

Thus, thanks to the connection adapter according to the invention the supply line area between the two shut-off valves and the device proper and, in addition, the permeate inlet line leading to the feed container can be included in each disinfection of the device, so that this cause of risk found in the former connection system and regarding the purity of the fluid components is eliminated.

The second supply line section of the adapter, which is not connected to the water inlet line of the device, but to a suitable different line, may be connected to an intermediate line section which is connected to the said other line and in which a shut-off valve should be arranged. If desired, the shut-off valve of the intermediate line section is able to suppress the supply of permeate through said line, so that permeate is only supplied through the second supply line section connected to the water inlet line of the device. If the shut-off valve in the intermediate line section remains open during permeate supply, permeate is supplied through both second line sections, which may be expedient whenever said other line also terminates in the feed container of the device. In a disinfecting process, the shut-off valve is opened in the intermediate line section, so that the disinfection fluid can flow through the intermediate line section, the second supply line section connected thereto and through the other second supply line section following said Y-member and through the water inlet line.

In more details it is suggested that the quick-action coupling member should be part of a water-tight housing in which the pressure sensor and the two shut-off valves are accommodated. A compact structure of the adapter according to the invention is thereby achieved.

The shut-off valves are preferably position-monitored solenoid valves which are actuated via the device. In the currentless state the solenoid valves are preferably closed. This is the case in the operative phase "disinfection". Before each treatment and each disinfection of the device the position of the two shut-off valves of the adapter will be checked automatically.

The two solenoid valves form a redundant system which prevents disinfection solution from flowing back into the permeate ring line (or possibly a single connection line).

Further details and features of the invention become apparent from the following description of preferred embodiments and from the drawings, of which FIG. 1 is a purely schematic illustration of an adapter according to the invention; and FIG. 2 shows the line system of a dialysis device with the connection system according to the invention.

The adapter according to the invention contains a quick-action coupling member 1 which can be coupled rapidly and easily to an associated quick-action coupling member 2 of a permeate line 3. The quick-action coupling member 1 is mounted at the end of a first supply line section 4 which contains downstream thereof a pressure sensor 20 and two successively arranged 2/2-way valves 5 and 6 with which the flow through the first supply line section 4 can be selectively enabled or disabled. The two 2/2-way solenoid valves form a redundant protection system for the permeate line 3.

Two second supply line sections 8, 9, which are formed by hoses, are connected to a Y-branching member 7 mounted on the other end of the first supply line section 4.

The quick-action coupling 1, 2 is made from special steel. Power supply to and control of the solenoid valves 5, 6 are carried out via the dialysis device. In the currentless state the solenoid valves 5, 6 are closed.

Figure 2:
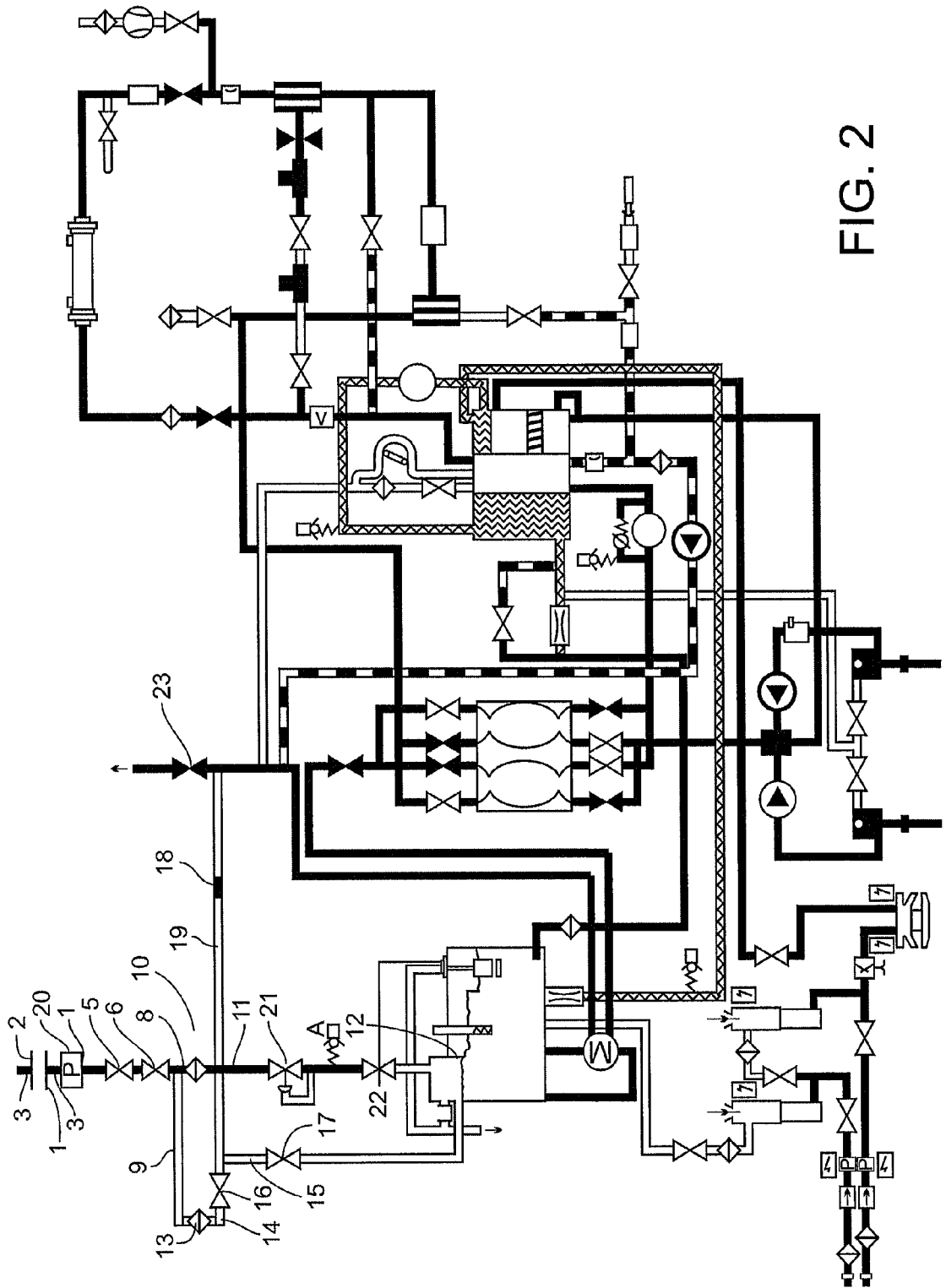

FIG. 2 shows the connection of the adapter according to FIG. 1 to a conventional dialysis device. The supply line section 8 is connected via a hose clip 10 to the permeate inlet line 11 of the device which is provided with two successive valves 21 and 22 and terminates in the feed container 12 of the device.

The other second supply line section 8 is connected via a hose clip 13 to an intermediate line section 14 which in turn is in communication with a fluid line 15 of the device, which also terminates in the feed container 12.

The intermediate line section 14 contains a shut-off valve 16. A shut-off valve 17 is also interposed in line 15.

The solenoid valve 16 interposed in the intermediate member 14 is arranged such that the existing functions are thereby not changed in the dialysis device. In the operative phase "dialysis", the permeate inlet via connection 10 into the feed container 12 for permeate is maintained by closing valve 16.

In the operative phase "disinfection", disinfection fluid flows in the direction of arrow 18 through line 19. The disinfection fluid is alternately circulating through line 15 into the feed container 12 and through the intermediate member 14, the supply line sections 9 and 8 and through the permeate inlet line 11 into the feed container 12 by alternately switching valves 16 and 17. The closed solenoid valves 5 and 6 prevent disinfection fluid from flowing back into the permeate ring line.

When the solenoid valve 16 is closed in the operative phase "dialysis", free inflow of the permeate through the supply line section 8 is guaranteed.

When a dialysis device is used for performing an extracorporeal dialysis treatment, a distinction is made between three operative phases:

Standby
Dialysis
Disinfection

These three operative phases shall be described in more detail hereinafter in connection with the present invention.

Standby

In this operative state the two valves 5 and 6 are closed. Permeate from the most recent flushing process for the dialysis device is present in the lines between the adapter and the dialysis device. Hence, there is no risk for patients who are dialyzed at other dialysis places on the same permeate line.

Dialysis

The operative dialysis phase begins with the test $T_0$ of the dialysis device. This test includes the functional elements of the adapter. The valves 5 and 6 are here checked for operability by the valve positions being tested one after the other. A tightness check is here carried out at the same time. The pressure sensor 20 is also checked by carrying out a back-pressure and flow-pressure measurement. The flow pressure measurement is compared with the measurement of the reduced water inlet pressure at A (FIG. 2) behind valve 21. In consideration of a corresponding tolerance the two pressure values must be identical. If the deviation is too great, an error is indicated. If the two pressure values are close together, the $T_0$ test will be continued. If in this measurement the flow pressure is below the desired input pressure of the dialysis device, a water shortage alarm will be initiated via valve 21. As a consequence, the dialysis device cannot complete the $T_0$ test and does thus not start the operative dialysis phase proper. If the flow pressure is adequate, the $T_0$ test will be continued. After the $T_0$ test has been completed, valves 5 and 6 are opened. Valve 16 is closed. After valves 21 and 22 have been opened, permeate flows into the feed container. This further ensures the free inflow in the operative dialysis phase.

Disinfection

After the dialysis treatment the dialysis device is disinfected as a rule. With the use of the adapter the permeate line is to be included in each disinfection. A distinction is made in the dialysis device between the disinfection types thermal disinfection, chemo-thermal disinfection and chemical disinfection. It is regarded as a risk for all of the listed disinfection types that a backflow of disinfection solution might occur via the adapter into the permeate line during or after disinfection. This is possible when the pressure prevailing in the dialysis device is higher during opening of valves 5 and 6 than the pressure prevailing in the permeate line. After the operative phase disinfection has been selected, permeate flows via connection 10 into the dialysis device. Valves 21 and 22 are opened. Valve 16 is closed and valve 17 is opened. The flow pressure is measured in the pressure sensor 20 and compared with the measured pressure value behind valve 21. If both values are within the tolerance range, the disinfection process is continued. If the pressure at pressure sensor 20 in the adapter is smaller than the required flow pressure in the dialysis device, valves 5 and 6 are closed again. The dialysis device indicates a water shortage alarm. If the pressure sensor 20 records a sufficiently high pressure, valves 5 and 6 remain open and permeate can continue to flow into the dialysis device for disinfection. In this process permeate will only flow via connection 10 and valves 21 and 22. During disinfection the disinfection fluid is circulating via valve 17. At defined intervals valve 17 is closed and valve 16 is opened. Thus disinfectant can also flow via coupling 13 to the adapter and back again via connection 10 into the feed vessel. This process is repeated in the disinfection phase several times. Thus the permeate supply line to the dialysis device and the line section for permeate in the dialysis device are integrated into the disinfecting process.

At the end of the disinfecting process a valve 23 (FIG. 2) opens and the dialysis device is flushed and freed from disinfectant. For this process permeate must flow into the dialysis device. For this purpose valves 5 and 6 must open in the adapter. This will only take place if the pressure sensor 20 at the permeate connection of the adapter senses a predetermined minimum pressure which must clearly be above the pressure prevailing in the dialysis device. If this is the case, valves 5 and 6 are opened. Permeate will then flow by alternately opening and closing valves 16 and 17 via connections 10 and 13 into the dialysis device. This ensures that the permeate supply lines leading to the dialysis device are flushed free. After the flushing operation the dialysis device will again be brought into the operative dialyzing state.

The invention claimed is:
1. A medical device which is connectable to a water line for the supply of water or prepared water into the medical device, containing an adapter which comprises
   a first supply line section (4) with a terminal coupling member (1) for connection to the water line (3), said terminal coupling member being a quick-action coupling member, with
   a downstream pressure sensor (20) connected to said first supply line section (4) and with two downstream, successively arranged shut-off valves (5, 6) connected to said first supply line section (4) next to said downstream pressure sensor (20), wherein said pressure sensor (20) is located with said terminal coupling member (1) located on one side and said two shut off valves (5, 6) are located on the opposite side of the pressure sensor (20) in series, and two second supply line sections (8, 9) which branch off from the first supply line section (4) by means of a branching member (7) which is connected to said first supply line section (4) after said shut-off valve (5,6), wherein one of the second supply line sections (8) is connected via a connection (10) to a permeate inlet line (11) of the medical device that terminates in a feed container (12), and the other one of the second supply line sections (9) is connected via a connection (13) and a shut-off valve (16) to another fluid line (15) of the medical device into which a shut-off valve (17) is inserted and which also terminates in the feed container (12), wherein disinfection fluid can flow through the other fluid line (15) in a disinfecting process and the shut-off valves (16 and 17) are alternatingly switchable, so that disinfection fluid is alternately circulating through the fluid line (15) into the feed container (12) and through the second supply line sections (8, 9) and the permeate inlet line (11) into the feed container (12).

2. The medical device according to claim 1, characterized in that the other one of the second supply line sections (9) is connected via the connection (13) to an intermediate line section (14) that is connected to the other line (15).

3. The medical device according to claim 2, characterized in that the shut-off valve (16) is arranged in the intermediate line section (14).

4. The medical device according to claim 1, characterized in that the coupling member is part of a housing accommodating the two shut-off valves (5, 6).

5. The medical device according to claim 1, characterized in that the shut-off valves (5, 6) are solenoid valves which are actuated via the device and are also powered by the device.

6. The medical device according to claim 5, characterized in that the solenoid valves (5, 6) are closed in the currentless state.

7. The medical device according to claim 1, characterized in that means are provided for automatically checking the position of the two valves (5, 6) before each treatment and disinfection.

8. The medical device according to claim 1, characterized in that the medical device is a dialysis device.

\* \* \* \* \*